United States Patent
Hoang

(10) Patent No.: US 10,806,923 B2
(45) Date of Patent: Oct. 20, 2020

(54) PATIENT ELECTRICAL TREATMENT SYSTEM

(71) Applicant: Le Trinh Hoang, D.O., Inc., Arcadia, CA (US)

(72) Inventor: Le Trinh Hoang, Arcadia, CA (US)

(73) Assignee: Le Trinh Hoang, D.O., Inc., Arcadia, CA (US)

(*) Notice: Subject to any disclaimer, the term of this patent is extended or adjusted under 35 U.S.C. 154(b) by 38 days.

(21) Appl. No.: 16/248,233

(22) Filed: Jan. 15, 2019

(65) Prior Publication Data

US 2019/0143104 A1    May 16, 2019

Related U.S. Application Data

(63) Continuation-in-part of application No. 15/271,856, filed on Sep. 21, 2016, now Pat. No. 10,179,089.

(51) Int. Cl.
| | | |
|---|---|---|
| *A61N 1/14* | (2006.01) | |
| *A61H 39/00* | (2006.01) | |
| *A61H 39/08* | (2006.01) | |

(52) U.S. Cl.
CPC ............ *A61N 1/14* (2013.01); *A61H 39/002* (2013.01); *A61H 39/086* (2013.01)

(58) Field of Classification Search
CPC ....... A61N 1/0456; A61N 1/14; A61H 39/002
See application file for complete search history.

(56) References Cited

U.S. PATENT DOCUMENTS

| | | | |
|---|---|---|---|
| 3,957,053 | A | 5/1976 | Woo |
| 4,745,517 | A | 5/1988 | Pitts |
| 5,054,486 | A | 10/1991 | Yamada |
| 7,724,491 | B2 | 5/2010 | Ober et al. |
| 8,882,763 | B2 | 11/2014 | Stevenson et al. |
| 2003/0135241 | A1 | 7/2003 | Leonard et al. |

(Continued)

FOREIGN PATENT DOCUMENTS

| | | |
|---|---|---|
| CN | 202933214 | 5/2013 |
| CN | 105030527 | 11/2015 |

(Continued)

OTHER PUBLICATIONS

United States Patent and Trademark Office, U.S. Appl. No. 15/245,367, "Office Action Summary," dated Jul. 25, 2017, 16 pages.

(Continued)

*Primary Examiner* — Paula J Stice
(74) *Attorney, Agent, or Firm* — Jeffrey G. Sheldon; Katherine B. Sales; Cislo & Thomas LLP

(57) ABSTRACT

A kit for discharging electrons from a human comprises at least two electrically conductive electrodes. The electrodes are adapted for creating an electrical connection with skin of the human. There is an electrically conductive pad with electrically conductive pad wires, one for each electrode for connection to the respective electrode to the pad. Electrically conductive grounding wire is provided for electrically grounding the pad. The kit can comprise electrically conductive gel for use with the electrodes to enhance electrically conductivity. The kit is designed, when assembled and used to treat a human, for withdrawing excess electrons from the human for improved health.

14 Claims, 3 Drawing Sheets

(56) References Cited

U.S. PATENT DOCUMENTS

| | | | |
|---|---|---|---|
| 2005/0094348 A1 | 5/2005 | Hattori | |
| 2006/0058694 A1* | 3/2006 | Clark | G01R 5/28 600/509 |
| 2006/0235465 A1 | 10/2006 | Koo et al. | |
| 2008/0071232 A1* | 3/2008 | Ober | A61N 1/14 604/293 |
| 2015/0107022 A1 | 4/2015 | Al Yazdi et al. | |
| 2018/0254714 A1* | 9/2018 | Rangel | H01Q 1/248 |

FOREIGN PATENT DOCUMENTS

| | | |
|---|---|---|
| KR | 20120109705 | 10/2012 |
| RU | 157530 | 12/2015 |
| WO | 2006090475 | 8/2006 |

OTHER PUBLICATIONS

United States Patent and Trademark Office, U.S. Appl. No. 15/271,856, "Non-Final Office Action ," dated Feb. 20, 2018, 10 pages.

\* cited by examiner

# US 10,806,923 B2

PATIENT ELECTRICAL TREATMENT SYSTEM

CROSS-REFERENCE TO RELATED APPLICATION

This application is a continuation-in-part of U.S. Non-Provisional application Ser. No. 15/271,856, filed Sep. 21, 2016, now U.S. Pat. No. 10,179,089, and is hereby incorporated by reference in their entirety.

BACKGROUND

Mammals can have out of balance electron charge with adverse health consequences. Ober et al. U.S. Pat. No. 7,724,491 describes a system where a grounded plane is conductively coupled to a human to conduct the earth's negative surface charges of free electrons from the earth to the animal.

A problem with systems such as Ober is that only surface contact with a human is obtained. Moreover, it is applicant's experience that the usual condition of a human is there is an excess of electrons, so the Ober system transmits electrons in the wrong direction.

Other systems are described in:
CN105030527
CN202933214
KR20120109705
RU157530
US2005/0094348
US2015/0107022
U.S. Pat. No. 3,957,053
U.S. Pat. No. 4,745,517
U.S. Pat. No. 8,882,763
WO06090475

Accordingly, the present invention is directed to improvements that overcome disadvantages of prior art systems.

SUMMARY

The present invention is directed to a system that improves on the prior art systems, providing a deeper treatment and generally withdrawing excess electrons from a mammal, namely, a human.

In particular, a kit for discharging electrons from a human comprises at least two electrically conductive electrodes adapted for creating an electrical connection with skin of the human. There is an electrically conductive pad and optionally, electrically conductive pad wires for each electrode for electrical connection of each electrode to the pad. An electrically conductive grounding wire is provided for electrically grounding the pad. Thus the electrodes, pad wires, pad and the grounding wire, when assembled, allow excess electrons to be withdrawn from the human.

Preferably the kit includes electrically conductive gel for use with the electrodes.

Preferably the gel contains silver chloride. Also preferably a harmonics filter is included for connection to the grounding wire.

In the kit, at least one of the pad wires can be pre-connected to its respective electrode.

The invention also includes the method for treating a human with the kit of claim 1. In the method, an even number of electrodes are coupled to the skin of a human, with one of the pad wires electrically connected to each of its respective electrode, wherein one half of the electrodes are placed on each side of the humans' medial line. For example, one electrode can be placed in each of the legs of the human. In the method each pad wire is electrically connected to the pad and then the pad is connected with the grounding wire.

The invention also includes a system where the kit is assembled.

DRAWINGS

These and other features, aspects and advantages of the present invention will become better understood with reference to the following description, appended claims, and accompanying drawings where:

DESCRIPTION

Figure 1:
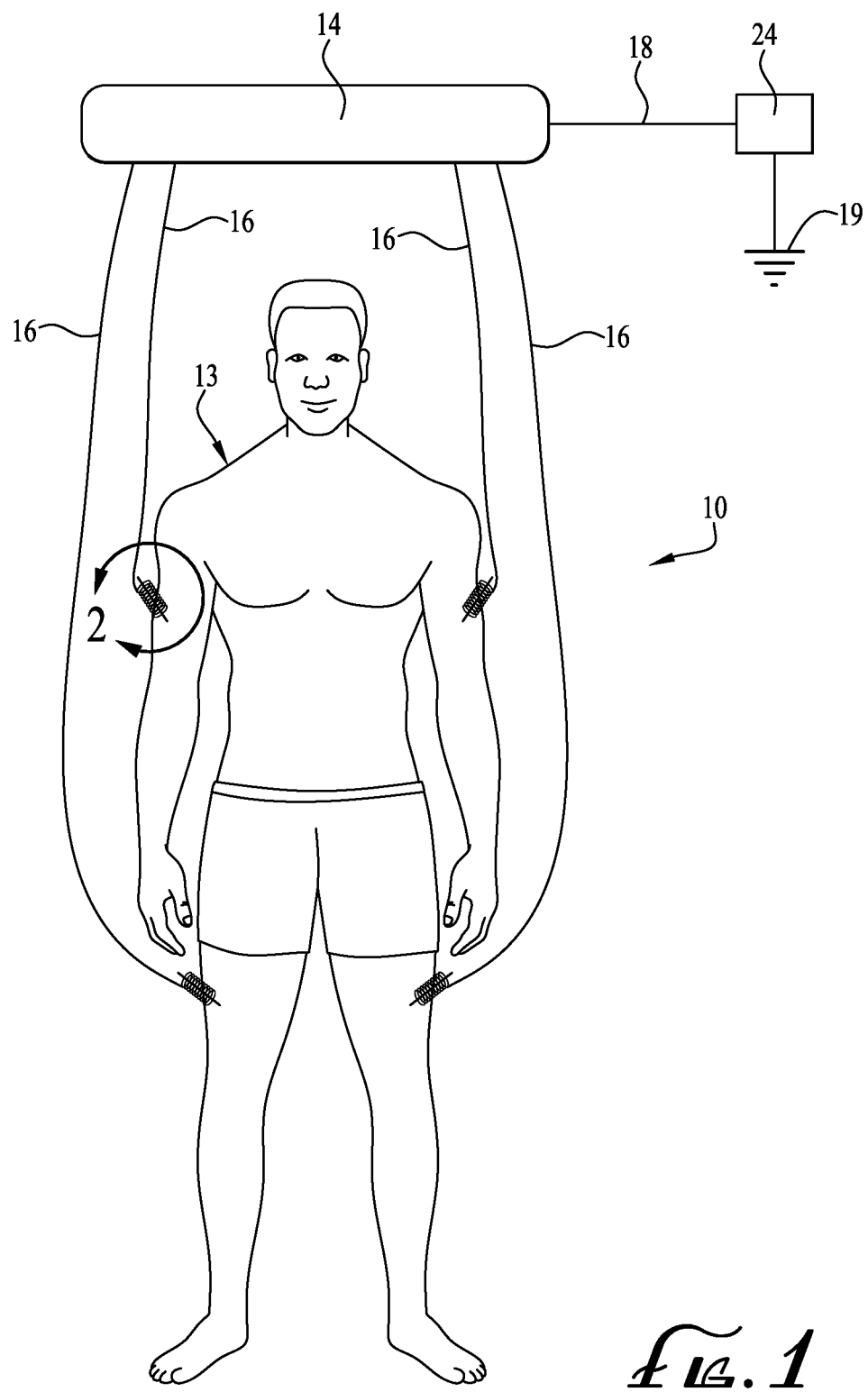
FIG. 1 is a schematic view of the system having features of the present invention being used for treating a mammal, namely a human.
Figure 2:
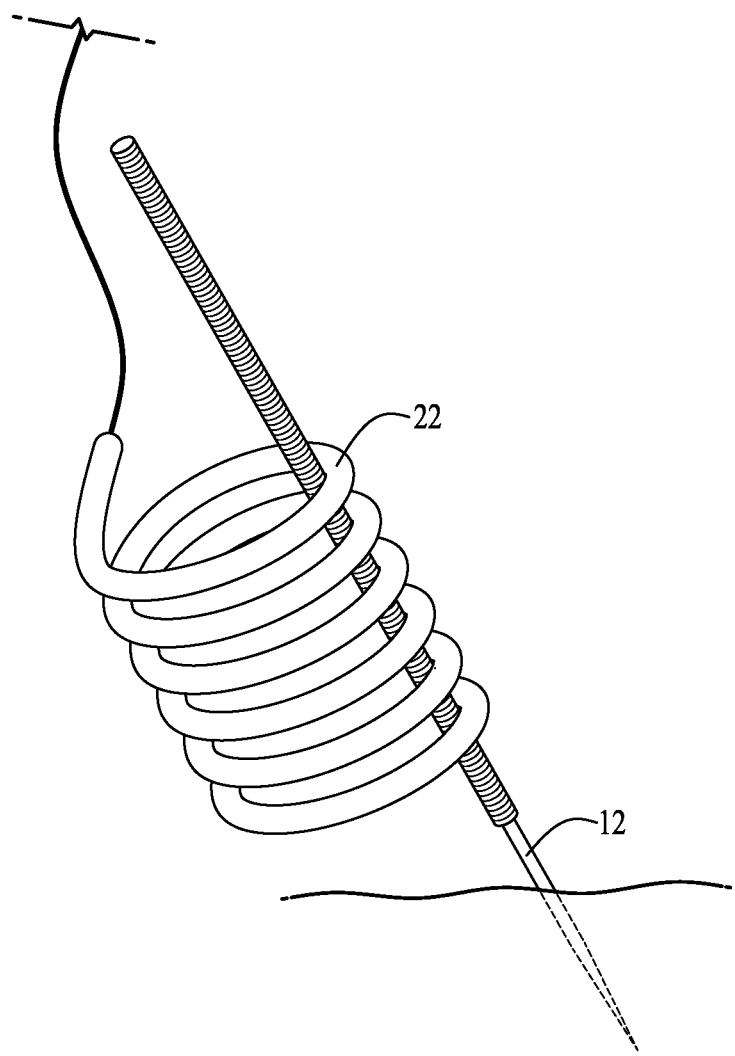
FIG. 2 is a perspective view of a portion of the system of FIG. 1.
Figure 3:
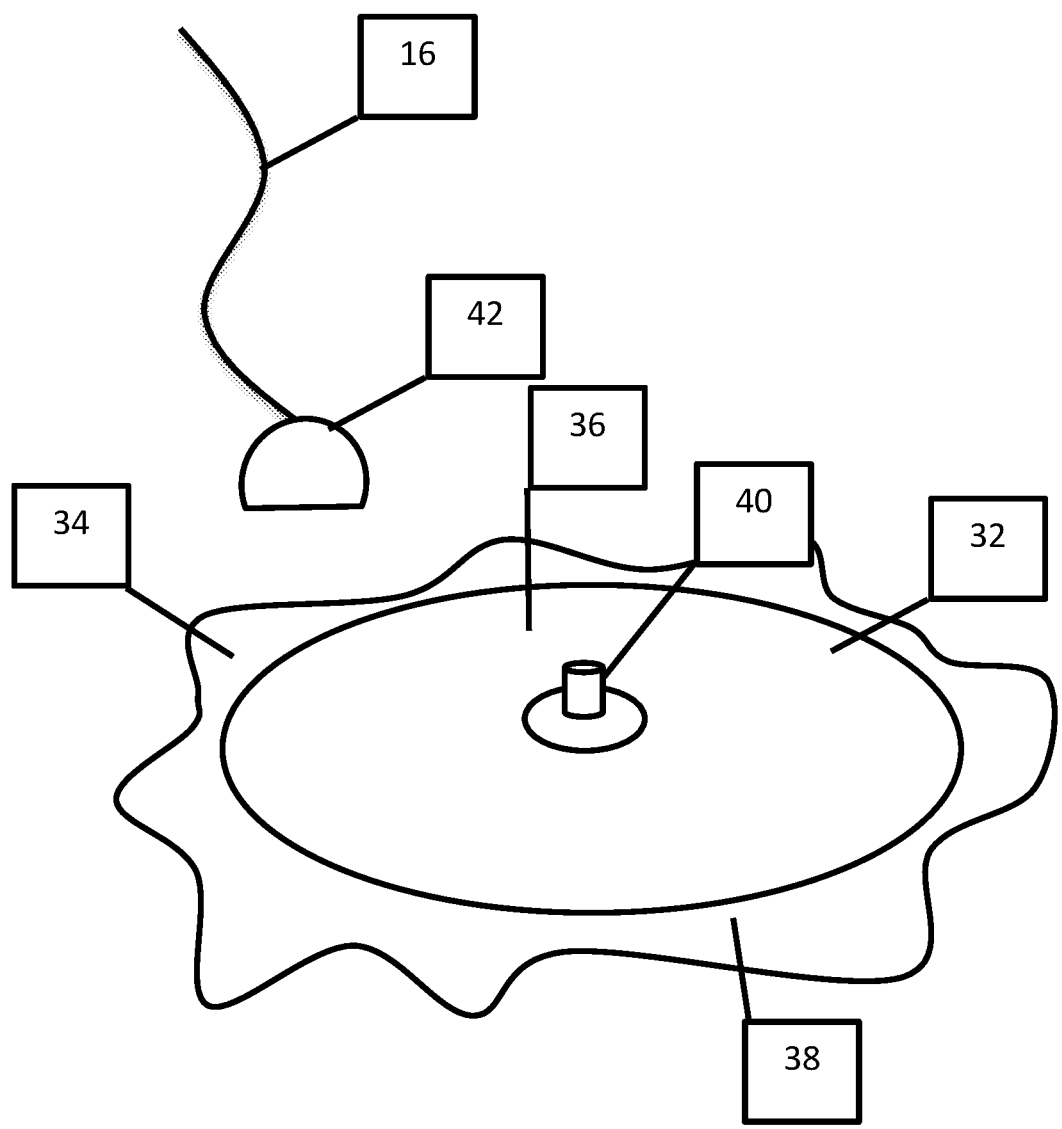
FIG. 3 is perspective view of an electrode and electrically conductive gel that can be used with the system of FIG. 1 in place of needles.

A system having features of the present invention is shown being used in FIG. 1, with FIG. 2 showing perspective close up view of a portion of the system. The system 10 comprises acupuncture needles 12, typically an even number, a patient 13, and an electrically conductive pad 14, also referred to as a grounded plane. Preferably the needles 12 are electrically connected to the pad 14 with electrically conductive pad wires 16, or less preferably, directly electrically connected to the pad with pad wires. The pad 14 is connected to ground with a grounding wire 18.

The term "electrically connected" (and similar terms such as "electrical communication") means that electron flow is possible between two structures with less resistance than provided by air. Electrical connection can involve direct physical connection, or can use an intermediary such as a conductive wire. For example, in the present invention the pad can be in physical contact with the needles or a pad wire can be connected to the pad and a needle (or coil as described below).

Typically, the acupuncture needles are thin metal needles adapted for creating an electrical connection with subcutaneous tissue of a mammal such as the human patient 13 as shown in FIG. 1. The invention is not limited to use for humans, but can be used with other mammals needing treatment.

Typically, the needles 12 are made of stainless steel, making them flexible, rust resistant and break resistant. The needles can be reusable or usable, if sterilized between use. The needles can a length of from about 13-130 mm with a diameter from about 0.16 mm to about 0.46 mm.

Because of the limited electrical conductivity of stainless steel, preferably, but optionally, each needle is provided with a helical copper coil 22 that is in electrical contact with the respective needle 12, with the pad wire 16 connect to the copper coil and the pad 14. The coil need not be made of 100% copper, but can be made of alloys where copper is the predominant compound, generally at least 90% by weight copper.

Optionally, instead of using needles 12 and coils 22, the system 10 can use one or more electrodes 32 and electrically conductive gel 34. The rest of the system 10 components remain the same. The electrode 32 is a conductive pad that can be removably attached, usually via adhesive, to the patient's skin 13, and conducts electricity out of the patient 13. The electrodes 32 are typically round, although they can be any shape, and are made from tape, cloth or a foam material, or other type of conformable material. An example of an acceptable electrode 32 is 3M Red Dot Tape EKG Electrode, manufactured by 3M, having a place of business in Maplewood Minn.

The electrode 32 has a top surface 36, a bottom surface 38, and an external coupler 40 coupled to the top surface 36. When the electrode 32 is attached to the patient 13, the bottom surface 38 is proximate the patient's skin 13. The external coupler 40 is a projection and couples to the pad wires 16. Preferably, each electrode 32 comprises a silver/silver chloride conductor embedded therein.

The gel 32 provides a highly conductive sealing layer between the electrode 32 and the patient 13 in order to increase the efficiency by which electricity travels from the patient 13. Preferably the gel 32 contains silver chloride to permit electron conduction from the patients 13 skin to the pad wires 16. The gel 32 is highly conductive and typically water soluble. Optionally, the gel 32 can also be bacteriostatic. Optionally, the gel 32 can come pre-applied to the bottom surface 38 of the electrode 32.

Preferably the electrodes 32 are electrically connected to the pad 14 with the electrically conductive pad wires 16, or less preferably, directly electrically connected to the pad with pad wires. As noted above, the pad 14 is connected to ground with a grounding wire 18. The pad wires 16 can comprise an electrode coupler 42 for coupling to the external coupler 40 on the electrodes 32. As noted above, the external coupler 40 is a projection and the electrode coupler 42 is a button that removably snaps onto the external coupler 40. Optionally, the external coupler 40 can be a tab extending off the electrode 32, and the electrode coupler 42 is a clamp that clamps onto the tab.

Typically, the pad wires 16 and the grounding wire 18 are insulated copper wires, single strand or multiple strands, such as four up to about fourteen gauge.

The grounding can be effected by using a typical three prong plug for insertion into a three prong outlet, where the neutral and hot prongs are shortened so that no power current can flow through any part of the device. The elongated grounding prong is used for grounding to an earth ground 19.

The grounding pad 14 can be any shape, such as an elongated strip, round, or rectangular. As stated in the aforementioned. Oder patent, such grounding pads can include a mesh layer substrate comprised of a plurality of silver fibers, such as silver coated nylon fibers, having a silver content typically comprising 5% of the fabric. This substrate can comprise 95% polyester, nylon or cotton and 5% silver-suffused monofilament nylon knitted into a conductive grid pattern. Although 5% silver fiber content is preferred, the grounding pad silver fiber content can vary, such as between 1% and 10% silver fibers. The pad 14 serves as a grounded plane.

An optional harmonics filter 24 is between the grounding pad 14 and ground. The harmonics filter 24 can be provided at the beginning of the grounding wire 18, between the ends of the grounding wire 18, or at the terminal end of the grounding wire 18. The filter 24 filters out harmonics. One type of filter is a Satic brand global energy saver ES120 filter available from Satic Incorporated located in Missoula, Mont. Another suitable filter is a Stetzerizer brand available from Stetzer Electric, Inc. Both types of filters filter out transients (electrical surges) and harmonics.

For ease in packing and shipment, the components of the system can be provided as a kit requiring assembly.

Preferably there is an even number of acupuncture needles 12 provided so that one half of the needles is placed on each side of the mammal's medial line, thereby providing electrical balance on both sides of the grounded patient 13. FIG. 1 shows four such needles 12, one in each upper arm of the patient 13 and one in each thigh of the patient 13. If electrodes 32 are used instead of needles 12, preferably electrodes 32 are placed in the same configuration described above for the needles 12, where an even number of electrodes 32 are coupled to the skin of a human, with one of the pad wires electrically connected to each of its respective electrode, wherein one half of the electrodes are placed on each side of the humans' medial line. For example, one electrode can be placed on each of the legs of the human. In the method each pad wire is electrically connected to the pad and then the pad is connected with the grounding wire.

It is found that this system when in use transmits electrons effectively from the patient to the ground. This is because in use the acupuncture needles have their ends placed subcutaneously in contact with the subcutaneous fluid of the mammal, which provides much more effective electron transfer than trying to adjust the electrical balance of a patient using only contact with the epidermis.

A kit can be provided with certain components preconnected such as having the pad wires connected to their respective needles such as by the pad wires pre-connected to the helical coils. Optionally, instead of needles 12, the kit can be provided with the pad wires 16 being pre-connected to their respective electrodes 32.

Although the present invention has been described with regard to certain preferred versions hereof, other versions are possible. For example, the pad wires 16 need not be used, where the pad 14 is in direct electrical conduct with the coils and/or needles, or optionally the electrodes 32. Also the present invention can be used in conjunction with the system of Ober et al. U.S. Pat. No. 7,724,491. Therefore, the scope of the appended claims should not be limited to the preferred embodiments described herein.

What is claimed is:

1. A kit for discharging electrons from a human comprising:
    a) at least two electrically conductive electrodes adapted for creating an electrical connection with skin of the human;
    b) an electrically conductive pad for electrical communication with electrodes;
    c) an electrically conductive grounding wire for electrically grounding the pad; and
    d) a harmonics filter for connection to the grounding wire.

2. The kit of claim 1 comprising an electrically conductive gel for use with the electrodes.

3. The kit of claim 2 comprising an electrically conductive pad wire for each electrode for connection of the respective electrode to the pad.

4. The kit of claim 3 wherein at least one of the pad wires is preconnected to its electrode.

5. The kit of claim 2 wherein the electrically conductive gel contains silver chloride.

6. The kit of claim 1 comprising an electrically conductive pad wire for each electrode for electrical connection of the respective electrode to the pad.

7. The kit of claim 6 wherein at least one of the pad wires is preconnected to its respective electrode.

8. A method for treating a human comprising the steps of:
    a) selecting the kit of claim 1;

b) placing an even number of the electrodes in contact with skin of the human, the pad wires electrically connected to the electrodes, wherein ½ of the electrodes is placed on each side of the human's medial line;

c) connecting the pad to ground with the grounding wire; and d) placing the harmonics filter between the grounding wire and ground.

9. The method of claim 8 wherein the kit comprises an electrically conductive pad wire fix each electrode for electrical connection of the respective electrode to the pad, and the method comprises the additional step of electrically connecting each pad wire to the pad.

10. The method of claim 8 wherein the kit comprises an electrically conductive gel for use with the electrodes, and the method comprises the additional step of, prior to step b) applying gel to the skin of patient.

11. A system for discharging electrons from a human comprising:

a) at least two electrically conductive electrodes adapted for creating an electrical connection with skin of the human;

b) an electrically conductive grounded plane;

c) an electrically conductive grounding wire electrically grounding the plane; and d) a harmonics filter connected to the grounding wire.

12. The system of claim 11 comprising an electrically conductive gel for use with the electrodes.

13. The system of claim 11 comprising an electrically conductive plane wire for each electrode in electrically conductive connection to its respective electrode and the plane.

14. The system of claim 12 wherein the electrically conductive gel contains silver chloride.

* * * * *